(12) United States Patent
Sharifi-Mehr et al.

(10) Patent No.: US 11,618,135 B2
(45) Date of Patent: Apr. 4, 2023

(54) AUTOMATIC RATCHETING SCREWDRIVER

(71) Applicant: K2M, Inc., Leesburg, VA (US)

(72) Inventors: Amir Ali Sharifi-Mehr, Bloomingdale, NJ (US); Steven F. Krause, Oakland, NJ (US)

(73) Assignee: K2M, Inc., Leesburg, VA (US)

( * ) Notice: Subject to any disclaimer, the term of this patent is extended or adjusted under 35 U.S.C. 154(b) by 541 days.

(21) Appl. No.: 16/809,065

(22) Filed: Mar. 4, 2020

(65) Prior Publication Data

US 2020/0282530 A1 Sep. 10, 2020

Related U.S. Application Data

(60) Provisional application No. 62/813,915, filed on Mar. 5, 2019.

(51) Int. Cl.
*B25B 15/04* (2006.01)
*A61B 17/70* (2006.01)
*A61B 17/88* (2006.01)
*B25B 23/00* (2006.01)

(52) U.S. Cl.
CPC .......... *B25B 15/04* (2013.01); *A61B 17/7082* (2013.01); *A61B 17/8888* (2013.01); *B25B 23/0035* (2013.01)

(58) Field of Classification Search
CPC . B25B 15/04; B25B 23/0035; A61B 17/7082; A61B 17/8888
USPC ............................................................ 81/32
See application file for complete search history.

(56) References Cited

U.S. PATENT DOCUMENTS

| 366,439 A | * | 7/1887 | Troy | ................... B25B 13/463 |
| | | | | 81/439 |
| 3,584,667 A | | 6/1971 | Reiland | |
| 4,197,889 A | | 4/1980 | Peterson | |
| 5,171,117 A | | 12/1992 | Seidl | |
| 5,423,819 A | | 6/1995 | Small et al. | |

(Continued)

FOREIGN PATENT DOCUMENTS

| EP | 1222899 A2 | 7/2002 |
| EP | 1293168 A2 | 3/2003 |

OTHER PUBLICATIONS

European Search Report for EP20160901 completed Aug. 14, 2020; 2 pages.

*Primary Examiner* — Hadi Shakeri
(74) *Attorney, Agent, or Firm* — Lerner, David, Littenberg, Krumholz & Mentlik, LLP

(57) ABSTRACT

A screwdriver for driving a screw in bone includes a first body configured to engage a tulip of the screw, a first central bore extending through the first body, a second body having a second central bore extending through the second body and an external surface having a spline member positioned at least partially within the cavity, an inner shaft configured to drive a screw into bone and being rotatably coupled with the second body, a spring-biased pawl engageable with the spline member of the second body, a collar rotatable relative to the first body and the second body and having a cammed inner surface, when the collar is rotated in a first direction about the first body, the cammed inner surface pushes the spring-biased pawl into engagement with the spline member to rotatably couple the first body and the second body.

17 Claims, 15 Drawing Sheets

(56) References Cited

U.S. PATENT DOCUMENTS

| | | |
|---|---|---|
| 5,553,983 A | 9/1996 | Shinjo |
| 5,649,931 A | 7/1997 | Bryant et al. |
| 5,836,430 A | 11/1998 | Vasudeva |
| 5,946,988 A | 9/1999 | Metz-Stavenhagen |
| 6,244,139 B1 * | 6/2001 | Huang ............... B25B 13/463 192/43.2 |
| 6,488,681 B2 | 12/2002 | Martin et al. |
| 6,554,834 B1 | 4/2003 | Crozet et al. |
| 7,311,022 B2 | 12/2007 | Putney et al. |
| 8,162,988 B2 | 4/2012 | Delecrin et al. |
| 8,460,307 B2 | 6/2013 | Saidha et al. |
| 8,545,505 B2 * | 10/2013 | Sandstrom ......... A61B 17/7085 606/86 A |
| 8,784,431 B1 | 7/2014 | Harder et al. |
| 8,845,652 B2 | 9/2014 | Heinz |
| 8,955,417 B2 | 2/2015 | Stiebitz et al. |
| 8,998,921 B2 | 4/2015 | Sharifi-Mehr et al. |
| 9,821,442 B2 | 11/2017 | Campbell |
| 9,867,639 B2 | 1/2018 | Biedermann et al. |
| 10,335,198 B2 | 7/2019 | Biedermann et al. |
| 10,385,902 B2 | 8/2019 | Wunderlich et al. |
| 2004/0138662 A1 | 7/2004 | Landry et al. |
| 2006/0036244 A1 | 2/2006 | Spitler et al. |
| 2006/0069391 A1 | 3/2006 | Jackson |
| 2006/0089644 A1 | 4/2006 | Felix |
| 2006/0111712 A1 | 5/2006 | Jackson |
| 2006/0293677 A1 | 12/2006 | Oepen |
| 2007/0288026 A1 | 12/2007 | Shluzas |
| 2008/0045970 A1 | 2/2008 | Saidha et al. |
| 2009/0264895 A1 | 10/2009 | Gasperut et al. |
| 2011/0313460 A1 | 12/2011 | McLean et al. |
| 2014/0276894 A1 | 9/2014 | Ramsay et al. |
| 2014/0276896 A1 | 9/2014 | Harper |
| 2019/0022833 A1 | 1/2019 | Macke et al. |

* cited by examiner

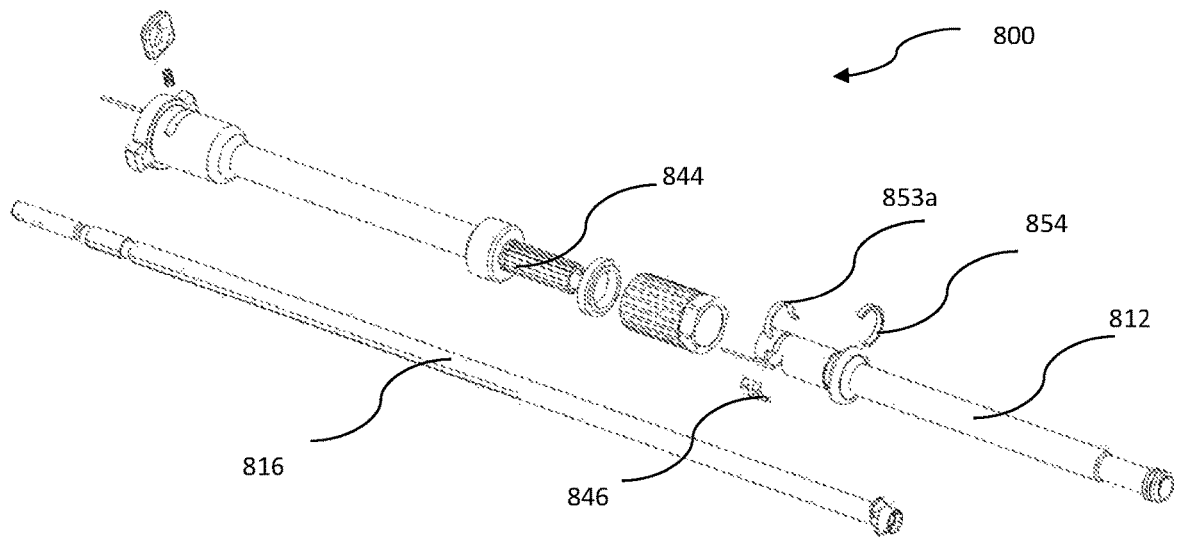
FIG. 21
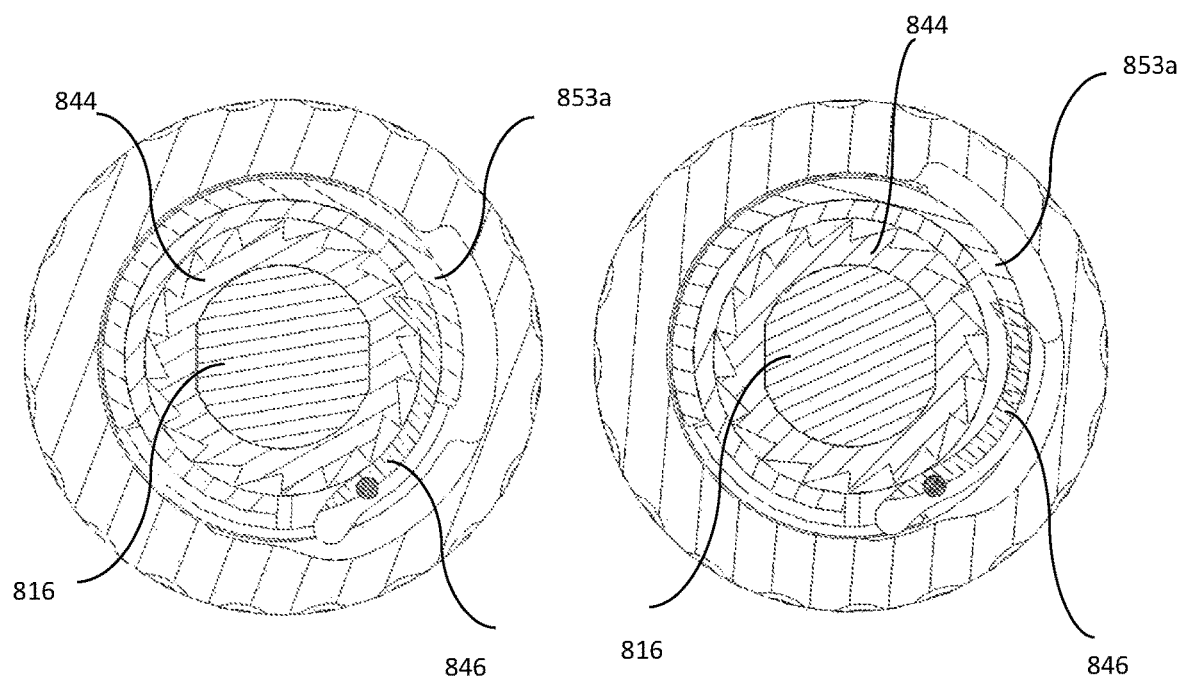
FIG. 22
FIG. 23

AUTOMATIC RATCHETING SCREWDRIVER

CROSS-REFERENCE TO RELATED APPLICATIONS

This application claims the benefit of the filing date of U.S. Provisional Patent Application No. 62/813,915 filed Mar. 5, 2019, the disclosure of which is hereby incorporated by reference herein.

BACKGROUND OF THE INVENTION

The present disclosure relates generally to spinal fixation devices and more specifically relates to a pedicle screw system having an improved screwdriver.

There are many types of spinal column disorders including scoliosis (abnormal lateral curvature of the spine), kyphosis (abnormal forward curvature of the spine), spondylolisthesis (forward displacement of one vertebra over another) and other disorders caused by abnormalities, disease, trauma, such as degenerative discs, slipped discs, etc.

In patients having conditions such as those described above, it is typical to employ a technique of spinal fixation to fuse vertebrae of the spine together or to alter the alignment of the spine. Spinal fixation often includes placement of pedicle screws. During surgery, the screws may be implanted with a screwdriver that has a lock to prevent loosening of the screw from the screwdriver. However, many of these locking devices are button locks or slide locks which require time and attention by the operator during the procedure. These types of mechanisms can also become unlocked during use of the screwdriver, often unintentionally so.

There exists a need for a screwdriver designed for secure handling for improved efficiency during surgery.

BRIEF SUMMARY OF THE INVENTION

According to an embodiment of the present disclosure, a screwdriver for driving a screw in bone includes a first body that has a first end configured to engage a tulip of the screw, a first central bore extending through the first body, and a cavity in communication with the first central bore and extending through a sidewall of the first body. The screwdriver includes a second body that has a second central bore extending through the second body and an external surface that has a spline member. The second body is positioned at least partially within the first central bore of the first body, such that the spline member is at least partially within the cavity of the first body. The screwdriver has an inner shaft positioned in the first and the second central bores that has a first end configured to drive a screw into bone. The inner shaft is rotatably coupled with the second body. A spring-biased pawl is disposed within the cavity of the first body and engageable with the spline member of the second body, and a collar is disposed on the first body and surrounds the spring-biased pawl. The collar is rotatable relative to the first body and the second body and has a cammed inner surface. When the collar is rotated in a first direction about the first body, the cammed inner surface pushes the spring-biased pawl into engagement with the spline member to rotatably couple the first body and the second body. The spring may be in the form of a c-clip spring.

In other embodiments, when the collar is rotated in a second direction about the first body that is opposite of the first direction, the pawl may disengage from the spline member such that the second body is rotatably decoupled from the first body. The pawl may have a hook-shaped first end configured to engage the spline member. The spline member may have a plurality of axial teeth configured to engage the pawl. The pawl may have a sinusoidal shape. The pawl may define a groove, and the screwdriver may include a spring received in the groove. When the second body is rotatably decoupled from the first body, the screwdriver may be in an unlocked condition in which the spring contacts the collar. When the collar is turned in the first direction, the screwdriver may be in a locked condition. The second body may be engageable with a robotic end effector for robotically driving the screwdriver. The first body may be distal to the second body. The first body may include a screw selection button engageable with the inner shaft. When the screw selection button is disengaged from the inner shaft, the first body may be axially movable relative to the inner shaft. The screwdriver may be configured for use with reduction screws and standard screws. The screwdriver may be part of a kit that also includes a robot that has a robotic end effector engageable with the second body for robotically driving the screwdriver. A proximal end of the screwdriver may include a plurality of tabs for transmitting torque from the end effector to the screwdriver. The kit may include at least one of a standard pedicle screw and a reduction screw.

According to another embodiment of the present disclosure, a screwdriver for driving a screw in bone includes a first body having a first end configured to engage a tulip of the screw, a first bore extending through the first body, and a threaded portion formed of a plurality of axially extending cantilever tabs. The screwdriver includes a second body having a second bore extending through the second body. The second body is positioned at least partially within the first central bore of the first body. An inner shaft is positioned in the first and the second bores and has a first end configured to drive a screw into bone. The inner shaft is rotatably coupled to the second body. An internally threaded ring is positioned on the threaded portion of the first body, and a collar is disposed on the first body and surrounds the internally threaded ring and the threaded portion of the first body. When the collar is rotated in a first direction about the first body, the internally threaded ring engages threads of the threaded portion of the outer sleeve and forces the plurality of cantilever tabs to engage the first body to rotatably couple the first body and the second body.

According to another embodiment of the present disclosure, a screwdriver for driving a screw in bone includes a first body having a longitudinal axis, a first end configured to engage a tulip of the screw, a first central bore extending through the first body, and a plurality of fingers extending transverse to the longitudinal axis, each finger having a projection extending in a direction toward the central bore. The screwdriver includes a second body having a second central bore extending through the second body and an external surface having splines on a portion of the external surface, the second body being positioned at least partially within the first central bore of the first body, such that the projections are engageable with the splines of the second body. An inner shaft is positioned in the first and second central bores and has a first end configured to drive a screw into bone. The inner shaft is rotatably coupled with the second body. A collar is disposed on the first body and surrounds the plurality of fingers and the splines. The collar is rotatable relative to the first body and the second body. The collar has a cammed inner surface, and when the collar is rotated in a first direction about the first body, the cammed inner surface pushes the fingers such that the projections engage the splines of the second body to rotatably couple the first body and the second body.

BRIEF DESCRIPTION OF THE DRAWINGS

FIG. 21 is an exploded view of the screwdriver of FIG. 19;

FIGS. 22 and 23 are cross-sectional views of the locking mechanism of the screwdriver of FIG. 19 in locked and unclosed positions, respectively.

DETAILED DESCRIPTION

FIG. 1-12 show screwdriver 100 according to a first embodiment of the present disclosure for a robotic screwdriver. Screwdriver 100 extends between proximal end 102 and distal end 104. Distal end 104 is configured for securing to and engaging a screw, such as pedicle screw 10 shown in FIG. 3. Screwdriver 100 may be used with mono-axial pedicle screws, poly-axial pedicle screws, reduction screws, screws designed for minimally invasive surgeries (MIS screws), and other compatible screws.

Figure 3:
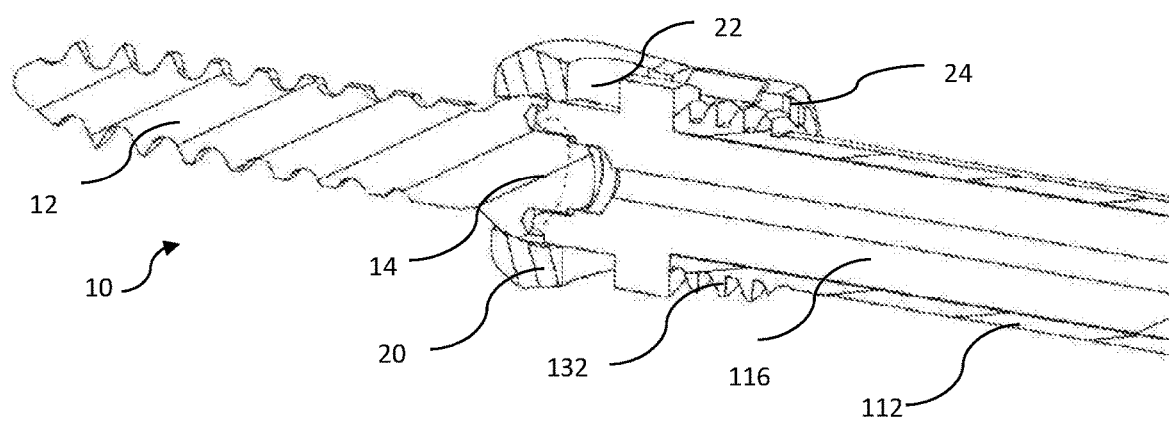
FIG. 3 is an enlarged cross-sectional perspective side view of the distal end of the screwdriver of FIG. 1.

FIG. 3 shows poly-axial bone screw 10 having a threaded shaft 12 and a head 14, received within a tulip 20. Tulip 20 is designed to receive a stabilizing rod therethrough. An inner surface 22 of tulip 20 includes threads 24 that engage with a set screw to secure the stabilizing rod and which are capable of engaging with the screwdriver 100, as described in further detail below.

Figure 1:
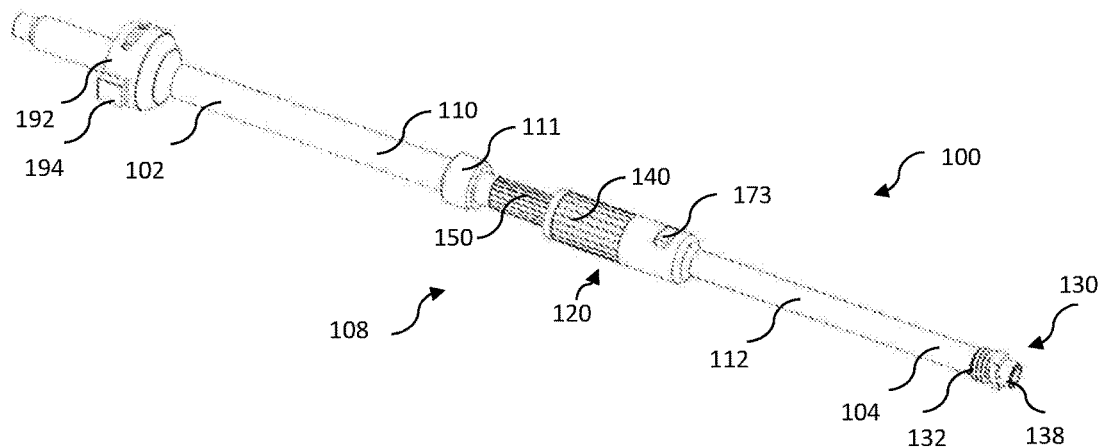
FIG. 1 is a perspective side view of a screwdriver according to a first embodiment of the present disclosure.
Figure 2:
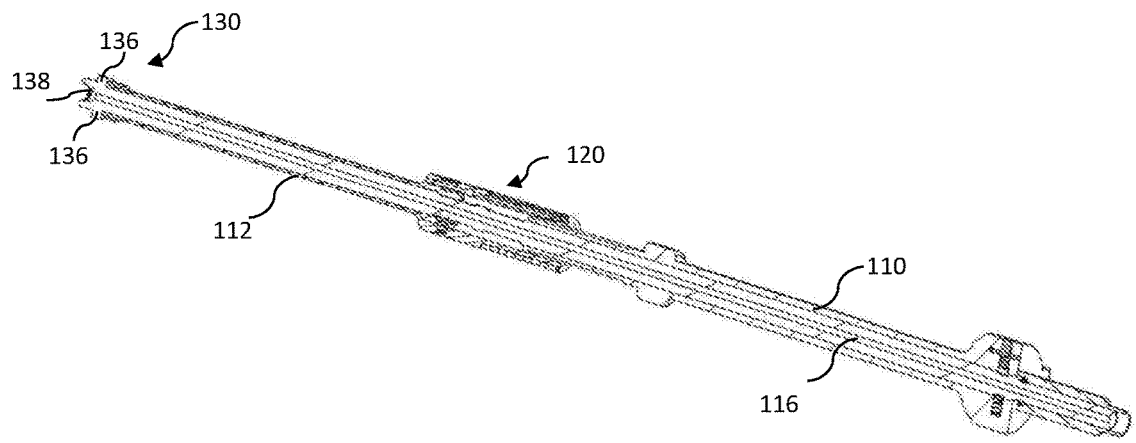
FIG. 2 is a cross-sectional perspective side view of the screwdriver of FIG. 1.

Referring to FIGS. 1-3, screwdriver 100 includes an outer body 108 formed of a proximal body 110, an outer sleeve 112 positioned distally to proximal body 110, and an inner shaft 116. Proximal body 110 and outer sleeve 112 each have a longitudinal bore extending completely therethrough along a central axis of each such that the bores share a common axis for receiving inner shaft 116. Inner shaft 116 is positioned concentrically within the outer sleeve 112 and proximal body 110.

At distal end 104, screwdriver 100 includes engaging end 130 for engaging screw 10. Outer sleeve 112 includes external threaded portion 132 configured to thread into corresponding threads 24 on inner surface 22 of the tulip 20 of screw 10. Shaft 116 includes driving member 138 for engagement within a corresponding opening of head 14 of screw 10 that resides within tulip 20. Driving member 138 may be hexagonally shaped or another non-circular shape and is designed to torque shaft 12 to advance screw 10 into bone. With shaft 116 positioned within outer sleeve 112 during use, driving member 138 extends farther distally than threaded portion 132 of the outer sleeve. Shaft 116 further includes at least two opposing lateral projections 136 abutted against threaded portion 132 of outer sleeve 112 for being received within tulip 20 of the screw 10, such that it has a non-circular cross section residing within tulip 20. Projections 136 also torque tulip 20 during advancement of screw 10 into bone so that screw 10 rotates all at once.

Screwdriver 100 includes an improved locking mechanism 135 that allows screwdriver 100 to automatically lock so that when screw 10 is threaded onto threaded portion 132 of outer sleeve 112, the screw cannot inadvertently loosen from outer sleeve 112 during use of screwdriver 100. Advantageously, this locking mechanism enables efficient locking and unlocking by a robotic device during operation.

Housing 120 interconnects outer sleeve 112 and proximal body 110. Locking mechanism 135 includes a collar 140 positioned around a ratchet assembly 143 for facilitating the locking and unlocking of screwdriver 100.

Collar 140 defines a bore extending therethrough so that inner shaft 116 is positioned therethrough. Collar 140 is rotatable in opposing first and second directions relative to outer body 108, i.e. outer sleeve 112 and proximal body 110. In the illustrated embodiment, collar 140 is designed to be rotated in the first direction, e.g. clockwise direction, to lock screwdriver 100 and in the second direction, e.g. counterclockwise direction, to unlock screwdriver 100. Collar 140 includes an outer textured surface 142 for ease of gripping and rotating during use. Inner surface 144 of collar 140 is formed as a cam surface with a relief portion 147 to engage ratchet assembly 143, as described in further detail below.

Figure 4:
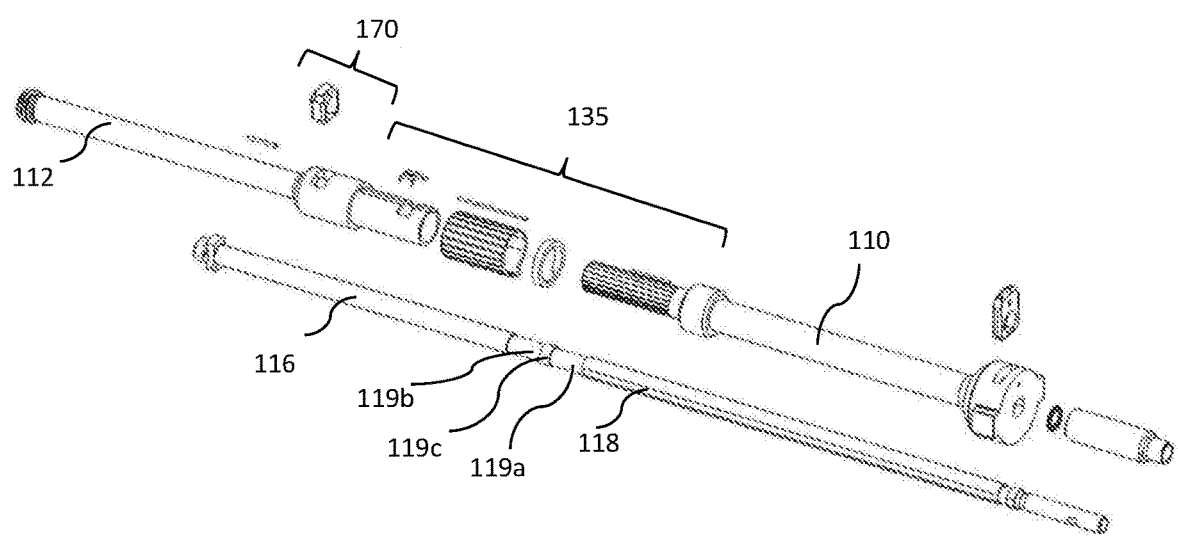
FIG. 4 is an exploded perspective side view of the screwdriver of FIG. 1.
Figure 5:
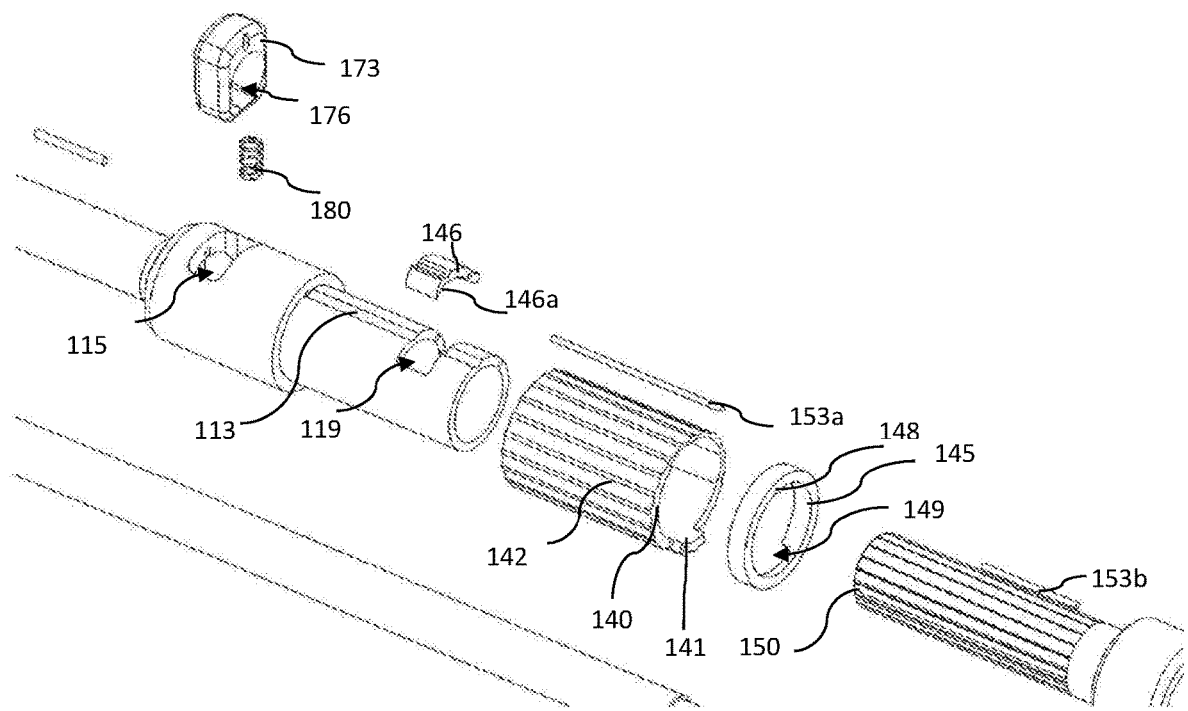
FIG. 5 is an enlarged view of FIG. 4.
Figure 6:
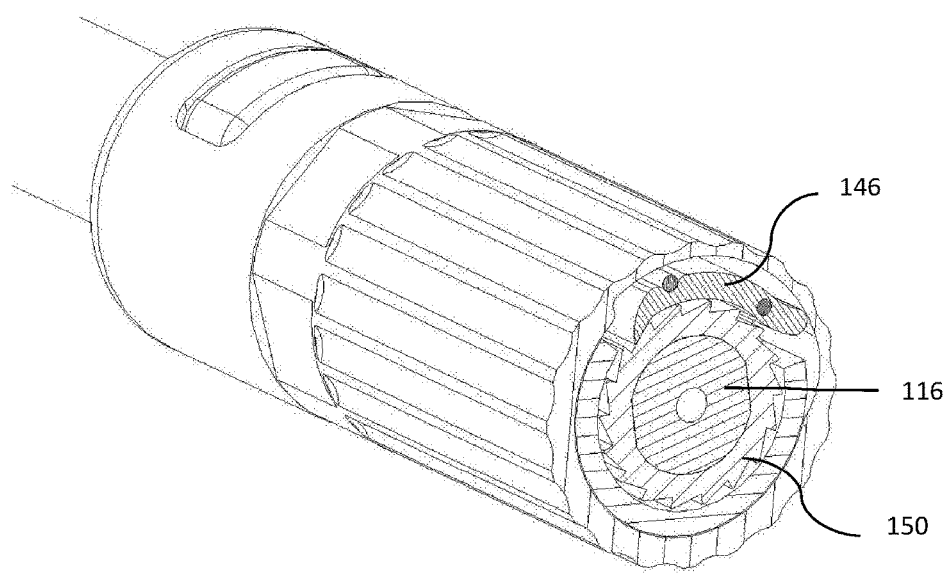
FIGS. 6 and 7 are perspective side and cross-sectional end views, respectively, of the locking mechanism of the screwdriver of FIG. 1 in a locked position.
Figure 7:
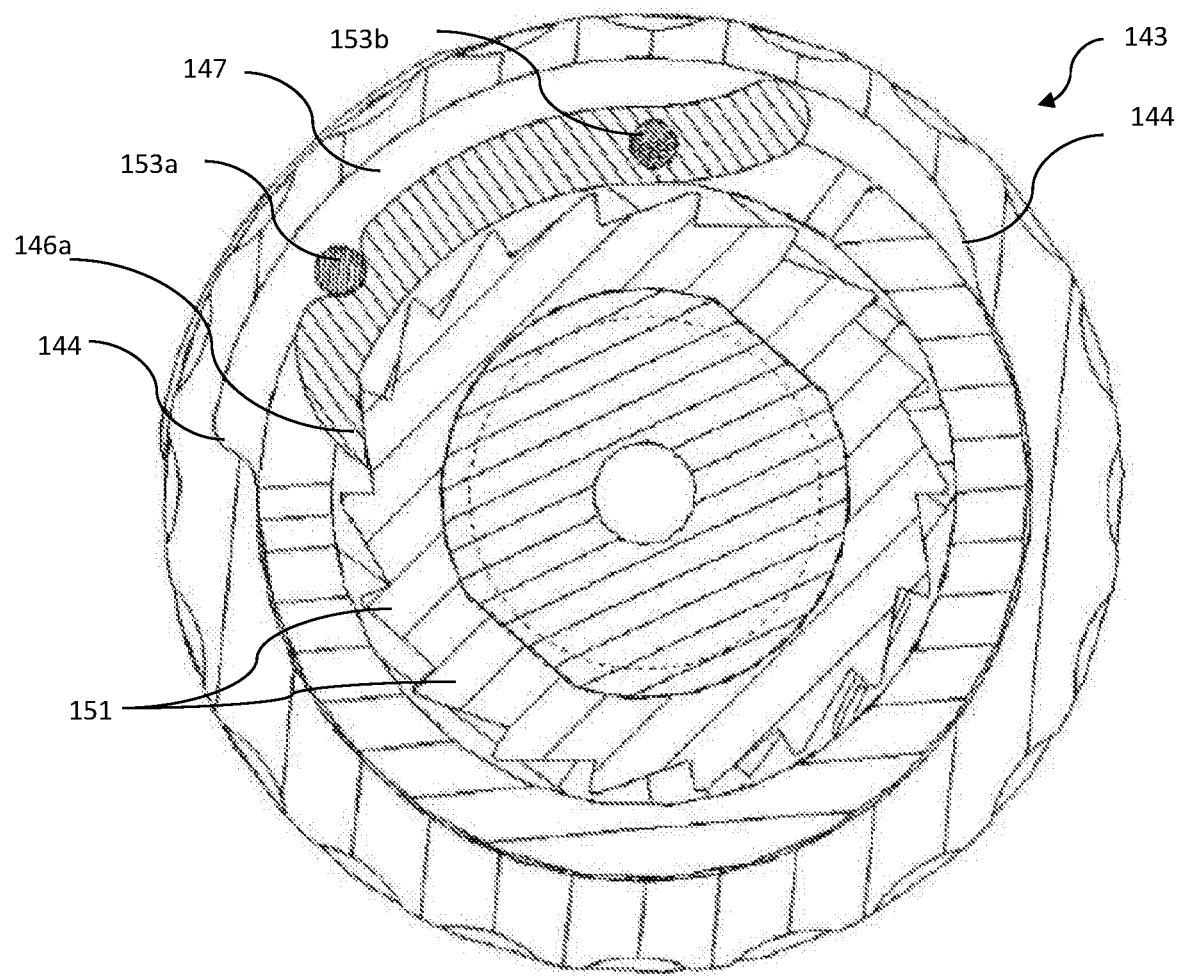

Ratchet assembly 143 includes spline member 150 formed on an external surface of proximal body 110. Spline member 150 defines a bore extending therethrough so that shaft 116 extends through the spline member. As shown in FIG. 4, shaft 116 is keyed, i.e. noncircular in cross section, such that it includes at least one flat surface 118 along a length of the shaft to prevent rotation of the shaft relative to spline member 150. Spline member 150 is similarly keyed and includes a plurality of axial splines or teeth 151, each being angled relative to a plane normal to the external surface of proximal body 110. Ratchet assembly 143 further includes pawl 146 positioned within opening 119 of outer sleeve 112. Pawl 146 includes a ramped portion 146a shaped as a hooked end and sized to correspond to the angled shape of splines 151 so that pawl 146 can engage splines 151 and a tail at an opposing end of the pawl. Pawl 146 may have a sinusoidal shape or an arc shape. Ratchet assembly 143 further includes a leaf spring 153a for biasing pawl 146 to engage spline member 150. Spring 153a is positioned on an upper surface of pawl 146 and a pin 153b is positioned through the body of the pawl to maintain the position of the pawl.

After engaging end 130 of screwdriver 100 is coupled with head 14 of screw 10, collar 140 can be rotated in the first, clockwise, direction so that threaded portion 132 of outer sleeve 112 mates with the corresponding internal threads 24 of tulip 20 to thread screw 10 onto screwdriver 100. As collar 140 is rotated in this first direction, spring 153a applies a force on pawl 146 to engage pawl 146 with spline member 150 to mechanically connect the rotation of the outer sleeve 112 and the spline member 150 of the proximal body 110. Because inner shaft 116 is rotationally fixed to spline member 150, due to the keyed surface of inner shaft 116, outer sleeve 112 is mechanically connected with inner shaft 116 in this configuration, shown in FIGS. 6 and 7.

The engagement of pawl 143 and spline member 150 places the screwdriver 100 in a locked condition so that outer body 108 and inner shaft 116 are in mechanical engagement with each other to prevent accidental or inadvertent unthreading of threaded portion 132 of outer sleeve 112 from threads 24 of tulip 20. When ratchet assembly 143 and thus screwdriver 100 is in the engaged or locked condition, the screw can then be advanced into bone without loosening from the screwdriver.

Screwdriver 100 further includes a limiting feature to prevent the collar from rotating further than necessary. In the illustrated embodiment, locking mechanism 135 further includes ring 145 that has a protrusion 148 projecting inward toward a center of the ring 145 and received within groove 113 of outer sleeve 112 to prevent ring 145 from rotating relative to the outer sleeve 112 when ring 145 is disposed about outer sleeve 112. Collar 140 includes projection 141 projecting in a proximal direction from a proximal end of collar 140. Projection 141 is sized and shaped to be received within a cut-out portion 149 on ring 145. The rotational movement of projection 141 is limited to the width of cut-out portion 149, which limits the amount that collar 140 can rotate once it has transitioned to the desired condition, i.e. locked or unlocked.

As a result of ratchet assembly 143, screwdriver 100 and locking mechanism 135 allow for relatively easy and intuitive unthreading of the screwdriver from screw 10 to remove the screwdriver after the screw has been implanted within bone.

Figure 8:
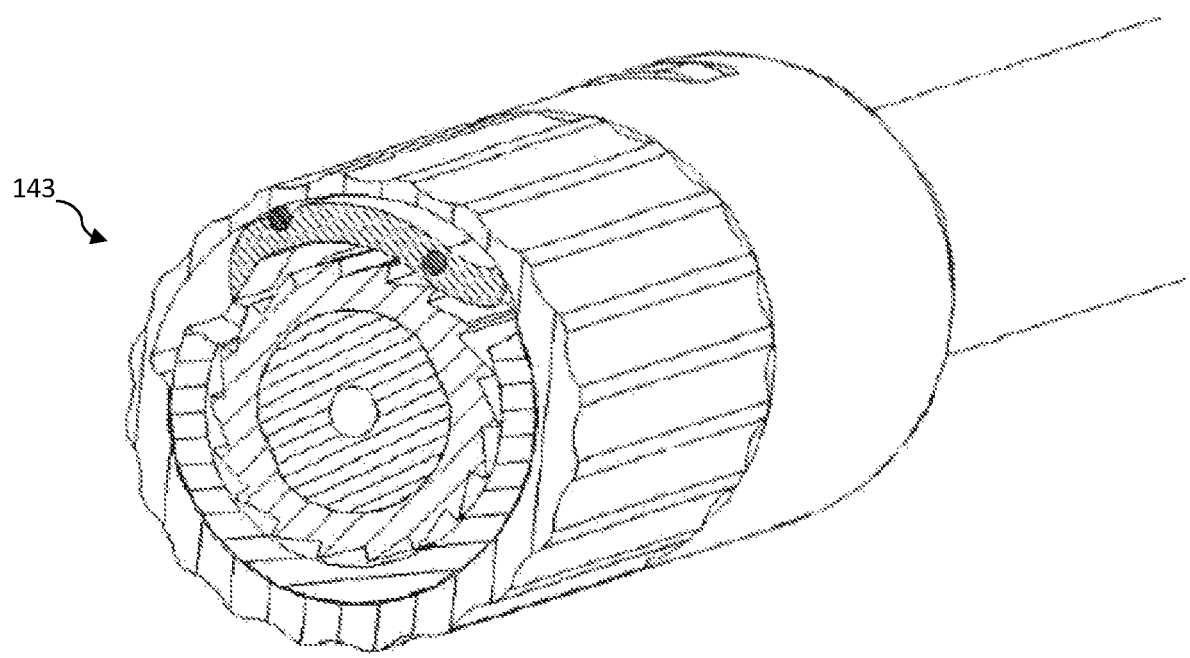
FIGS. 8 and 9 are perspective side and cross-sectional end views, respectively, of the locking mechanism of the screwdriver of FIG. 1 in an unlocked position.
Figure 9:
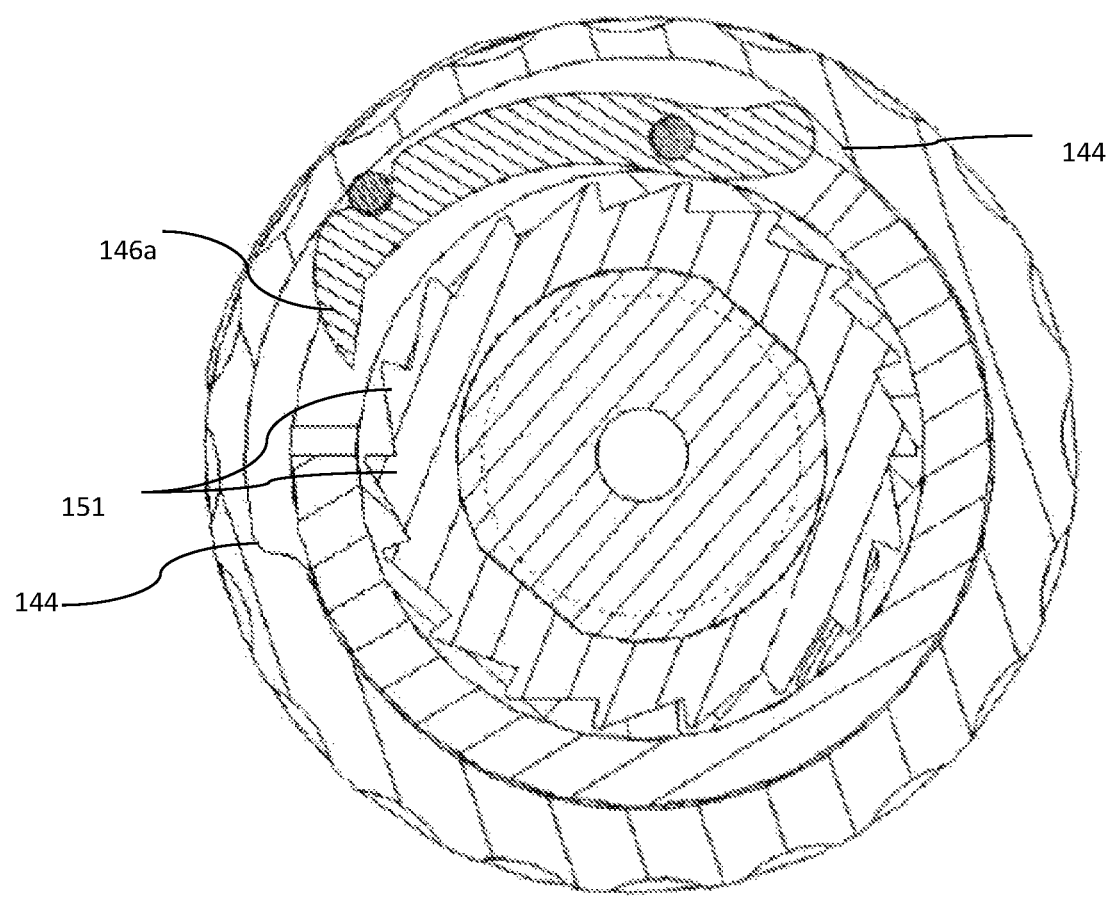
Figure 10:
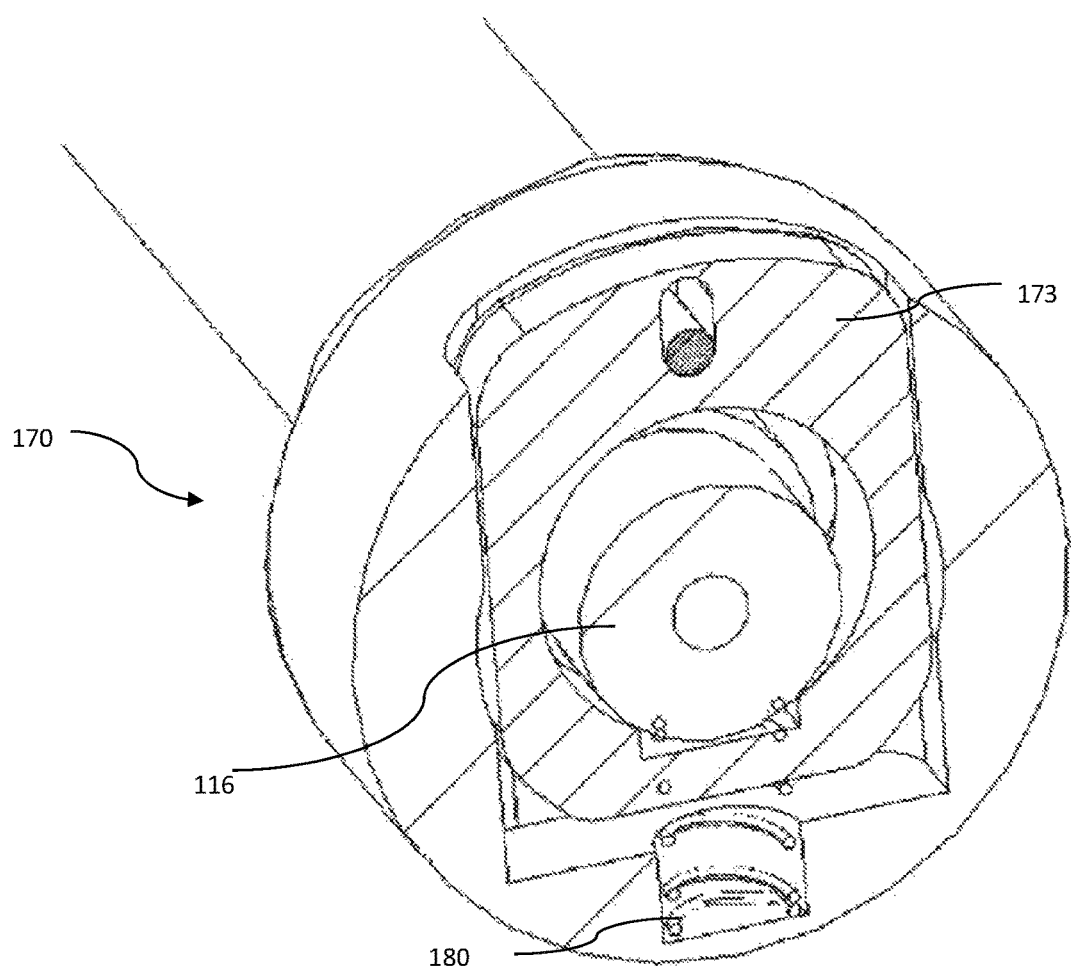
FIGS. 10 and 11 are cross-sectional perspective views of the screw selection mechanism of the screwdriver of FIG. 1.

Rotation of collar 140 in the second, counter-clockwise direction disengages pawl 146 from engagement with spline member 150, automatically placing the screwdriver in an unlocked condition, shown in FIGS. 8 and 9. This enables screwdriver 100 to move from the locked condition to the unlocked condition without the use of a button or other similar member resulting in a more efficient procedure. When ratchet assembly 143 and thus the screwdriver 100 are in the unlocked condition and the collar 140 continues to be rotated in the second, counter-clockwise direction, only outer sleeve 112 moves in this second direction, i.e. shaft 116 does not rotate. As outer sleeve 112 rotates in the second direction, the sleeve unthreads from tulip 20 without causing backing out of screw 10. This occurs when a tapered portion of the cam surface 144 contacts a tail of pawl 146, as shown in FIG. 9, to pivot pawl 146 out of engagement with splines 151. The rotation of outer sleeve 112 in the second direction forces this disengagement of pawl 146, which naturally allows outer sleeve 112 to rotate freely in the second direction about shaft 116.

Figure 12:
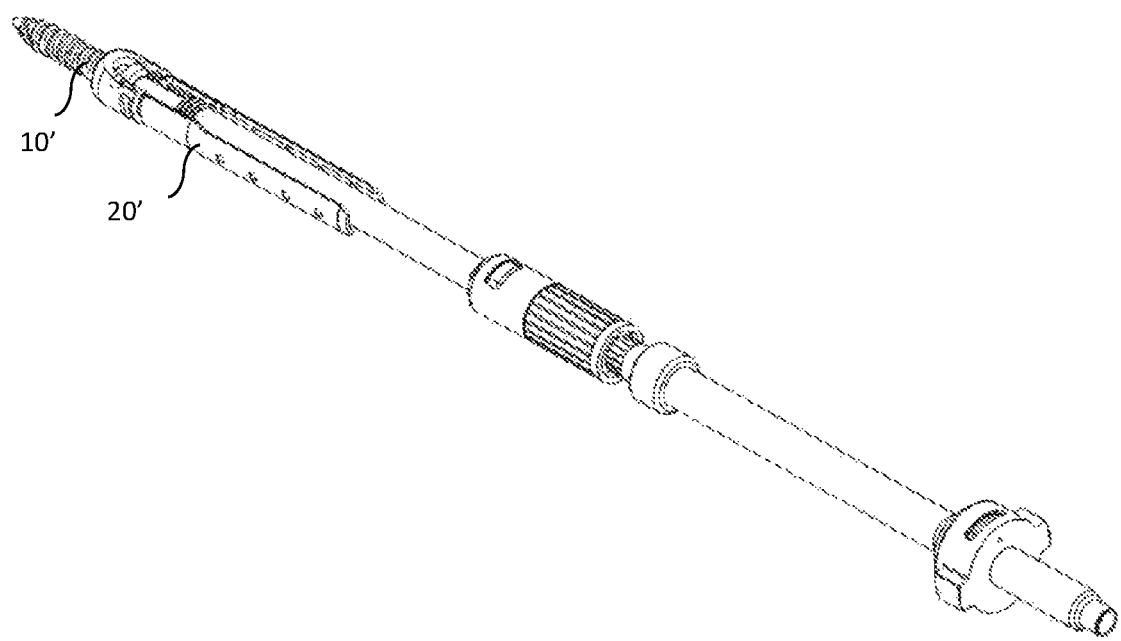
FIG. 12 is a side perspective view of the screwdriver of FIG. 1 in conjunction with a minimally invasive surgery screw.

Screwdriver 100 further includes screw selection mechanism 170 which allows the screwdriver to be used in conjunction with standard size pedicle screws, such as screw 10, and screws 10' that have elongated tulips or tabs 20' connected to the tulip that extend proximally therefrom such as reduction screws or MIS screws, shown in FIG. 12.

Figure 11:
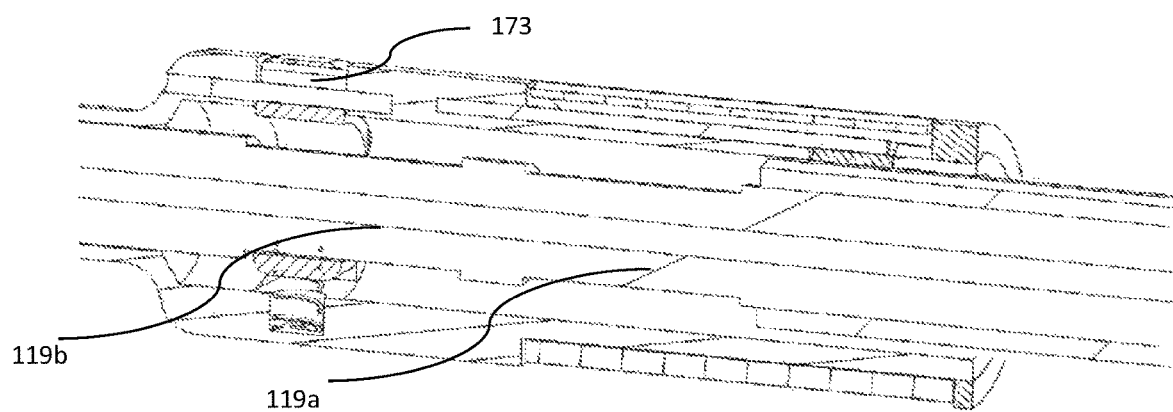

Screw selection mechanism 170 is housed within outer sleeve 112 and allows outer sleeve 112 to move axially relative to inner shaft 116 to change the longitudinal position of outer sleeve 112 relative to driving member 138 of inner shaft 116. As shown in FIGS. 4 and 11, inner shaft 116 has two zones along its length of reduced diameter. The first region of reduced diameter is region 119a which is positioned proximal to the second region 119b of reduced diameter of the shaft. The regions are separated by a region of relatively larger diameter 119c, which allows the two regions to be formed.

Screw selection mechanism 170 includes button 173 received within opening 115 of outer sleeve 112. Button 173 has a generally rectangular shape having two opposing rounded upper and lower surfaces. Button 173 further defines through-opening 176 for receiving inner shaft 116. Button 173 includes groove extending from proximal surface 178 to distal surface 179 that is open to through-opening 176. In a rest condition, button 173 is biased by spring 180 so that the spring maintains secure engagement with shaft 116 extending through button 173, and in the actuated condition, when button 173 is depressed by a user, spring 180 is compressed and outer sleeve 112 can be moved along its longitudinal axis. For example, if button 173 is positioned so that it is acting on region 119b of the shaft, outer sleeve 112 is positioned to receive a standard size screw. If rather than a standard size screw, a reduction screw is being used, the user may actuate screw selection mechanism 170 by depressing button 173 and sliding outer sleeve 112 in the proximal direction to region 119a so that the distance from the distal end of outer sleeve 112 to the distal end of inner shaft 116 is greater.

Figure 13:
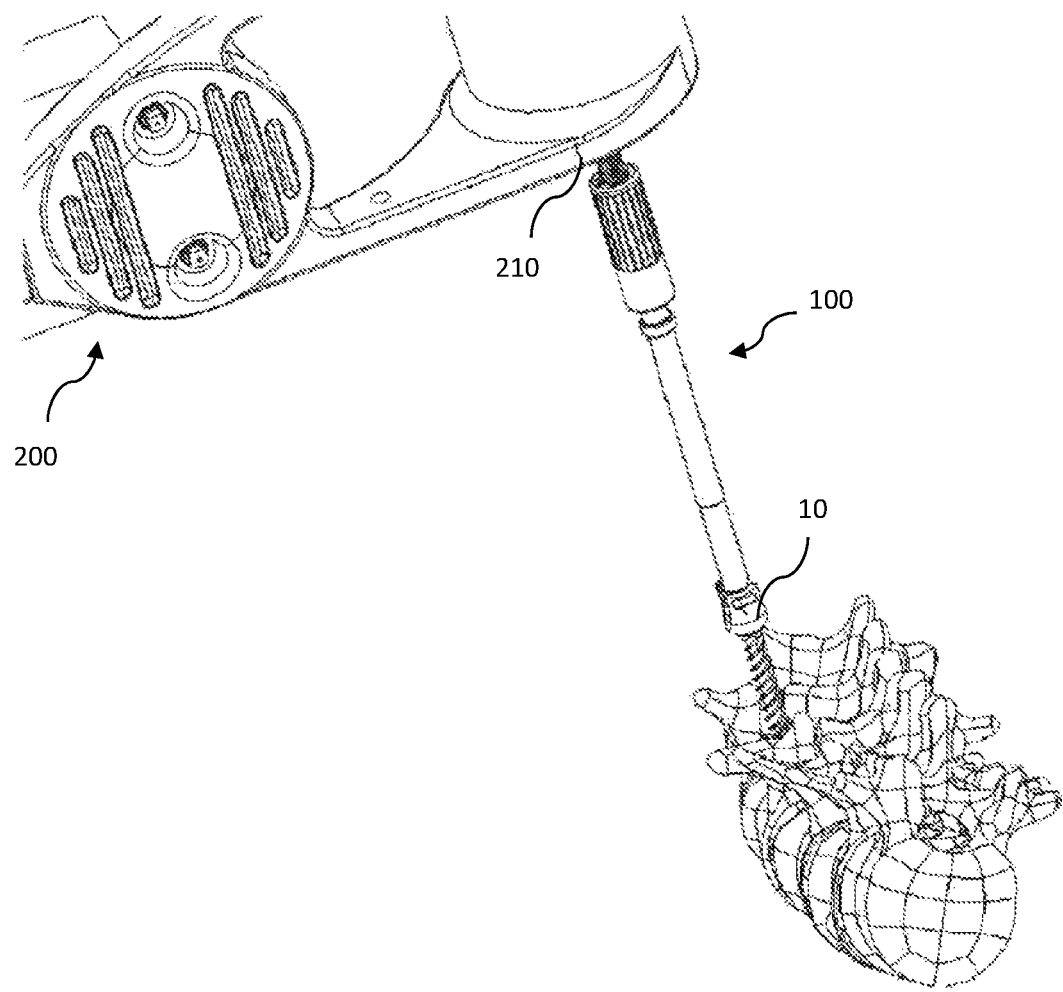
FIG. 13 is a schematic representation of the screwdriver of FIG. 1 in conjunction with a robotic device and a poly-axial screw.

Screwdriver 100 is designed for use in robot-assisted surgery. For example, as shown in FIG. 13, a robotic device 200 including a robotic arm with a rotatable end effector 210 coupled to the end of the robotic arm may interface with a robotic unit coupler 192 positioned on proximal end 102 of screwdriver 100. Robotic coupler 192 includes at least one tab 194 for transmitting torque to the screwdriver. Proximal body 110 includes shoulder 111 that has a relatively greater diameter to prevent run out of the driver during rotation. With inner shaft 116 positioned within outer body 108, the end effector 210 transmits torque to inner shaft 116 to advance the screw in bone. Though, in such a case, a surgeon or other user would engage locking mechanism 135 manually to lock the screw to the screwdriver prior to the use of the robot for screw advancement.

Robotic systems may be used throughout the pre-operative and intra-operative stages of the surgery. For example, preoperative planning for surgeries may include determining the bone quality in order to optimize bone preparation. Bone quality information, such as bone density or elastic modulus, can be ascertained from preoperative scans, e.g. CT scans. The bone quality data can be used to determine optimal properties for effective implant engagement. Examples of such methods are found in U.S. Pat. No. 10,166,109 to Ferko, filed on Sep. 18, 2014, entitled "Patient Specific Bone Preparation for Consistent Effective Fixation Feature Engagement," U.S. Patent Application Publication No. 2015/0119987 to Davignon et al., filed on Oct. 28, 2014, entitled "Implant Design Using Heterogeneous Bone Properties and Probabilistic Tools to Determine Optimal Geometries for Fixation Features," and U.S. Pat. No. 10,070,928 to Frank et al., filed on Jul. 1, 2015, entitled "Implant Placement Planning," each of which is hereby incorporated by reference herein in its entirety. In addition to preoperative imaging, robotic surgery techniques may employ imaging, such as fluoroscopy, during surgery. In such cases, systems integrating the surgical system with the imaging technologies facilitate flexible and efficient intraoperative imaging. Exemplary systems are described in U.S. Pat. No. 10,028,788 to Kang, filed on Dec. 31, 2013, entitled "System for Image-Based Robotic Surgery," hereby incorporated by reference herein in its entirety.

As in the instant case, robotic systems and methods may be used in the performance of spine surgeries to place implants in the patient's spine as in, for example, U.S. Patent Application Publication No. 2018/0325608 to Kang et al., filed on May 10, 2018, entitled "Robotic Spine Surgery System and Methods," the disclosure of which is hereby incorporated by reference herein in its entirety. The robotic system generally includes a manipulator and a navigation system to track a surgical tool relative to a patient's spine. The surgical tool may be manually and/or autonomously controlled. Examples of robotic systems and methods that employ both a manual and a semi-autonomous are described in U.S. Pat. No. 9,566,122 to Bowling et al., filed on Jun. 4, 2015, and entitled "Robotic System and Method for Transitioning Between Operating Modes," and U.S. Pat. No. 9,119,655 to Bowling et al., filed on Aug. 2, 2013, entitled "Surgical Manipulator Capable of Controlling a Surgical Instrument in Multiple Modes," each of which is hereby incorporated by reference herein in its entirety.

A robotic controller may be configured to control the robotic arm to provide haptic feedback to the user via the robotic arm. This haptic feedback helps to constrain or inhibit the surgeon from manually moving the screwdriver 100 beyond predefined virtual boundaries associated with the surgical procedure. Such a haptic feedback system and associated haptic objects that define the virtual boundaries are described in, for example, U.S. Pat. No. 9,002,426 to Quaid et al., filed on Jun. 23, 2008, entitled "Haptic Guidance System and Method," and U.S. Pat. No. 8,010,180 to Quaid et al., filed on Dec. 21, 2012, entitled "Systems and Methods for Haptic Control of a Surgical Tool," and U.S. Pat. No. 10,098,704 to Bowling et al., filed on May 18, 2016, entitled "System and Method for Manipulating an Anatomy," each of which is hereby incorporated by reference herein in its entirety.

In some cases of autonomous positioning, a tool center point (TCP) of a surgical tool, such as screwdriver 100, is brought to within a predefined distance of a starting point of a line haptic object that provides the desired trajectory. Once the tool center point is within the predefined distance of the starting point, actuation of an input causes the robotic arm to autonomously align and position the surgical tool on the desired trajectory. Once the surgical tool is in the desired position, the robotic system may effectively hold the rotational axis of the surgical tool on the desired trajectory by tracking movement of the patient and autonomously adjusting the robotic arm as needed to keep the rotational axis on the desired trajectory. Such teachings can be found in U.S. Patent Application Publication No. 2014/0180290 to Otto et al., filed on Dec. 21, 2012, entitled "Systems and Methods for Haptic Control of a Surgical Tool," which is hereby incorporated by reference herein in its entirety.

During operation of a robotic surgical system, the operation of the surgical tool can be modified based on comparing actual and commanded states of the tool relative to the surgical site is described in U.S. Patent Application Publication No. 2018/0168750 to Staunton et al., filed on Dec. 13, 2017, entitled Techniques for Modifying Tool Operation in a Surgical Robotic System Based on Comparing Actual and Commanded States of the Tool Relative to a Surgical Site," which is hereby incorporated by reference herein in its entirety. Further, robotic systems may be designed to respond to external forces applied to it during surgery, as described in U.S. Patent Application Publication No. 2017/0128136 to Post, filed on Nov. 3, 2016, entitled "Robotic System and Method for Backdriving the Same," which is hereby incorporated by reference herein in its entirety.

Further, because of the non-homogeneity of bone, applying a constant feed rate, a uniform tool path, and a constant rotational speed may not be efficient for all portions of bone. Systems and methods for controlling tools for such non-homogenous bone can be advantageous as described in U.S. Pat. No. 10,117,713 to Moctezuma de la Barrera et al., filed on Jun. 28, 2016, entitled "Robotic Systems and Methods for Controlling a Tool Removing Material From a Workpiece," which is hereby incorporated by reference herein in its entirety.

Figure 14:
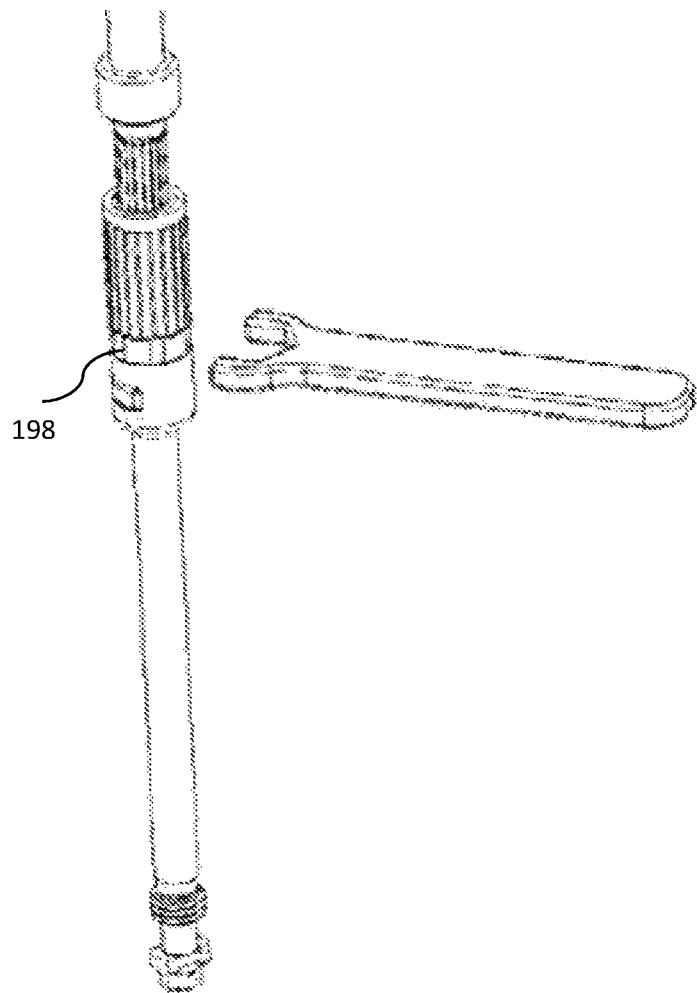
FIG. 14 is a perspective view of an alternative embodiment of a screwdriver according to another embodiment of the present disclosure.

In a variant example, shown in FIG. 14, screwdriver 100 includes hex member 198 on collar 140 or adjacent thereto to release the engagement of the ratcheting assembly 143 with the use of a wrench in the event there is an internal jam or the surgeon cannot otherwise effectively turn the collar counter-clockwise.

Figure 15:
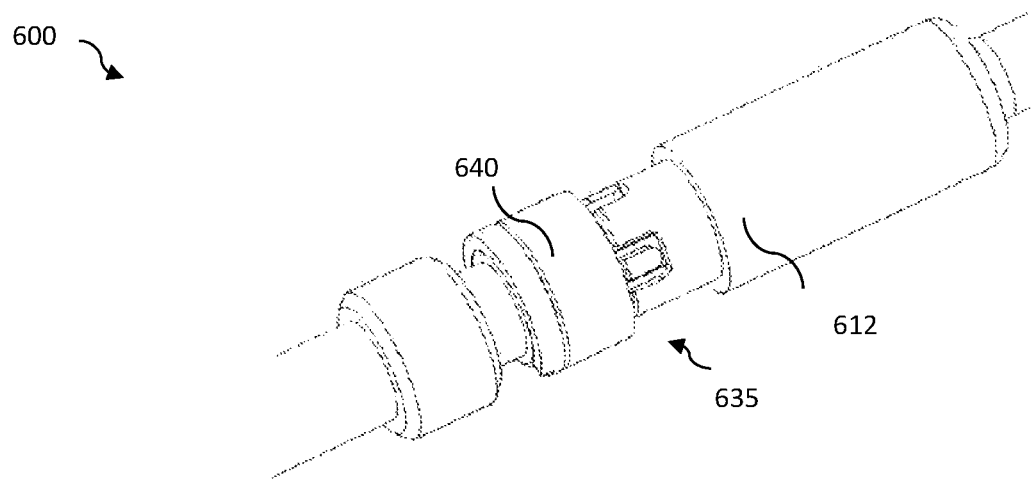
FIGS. 15 and 16 are perspective side views of another alternative locking mechanism according to an embodiment of the present disclosure.
Figure 16:
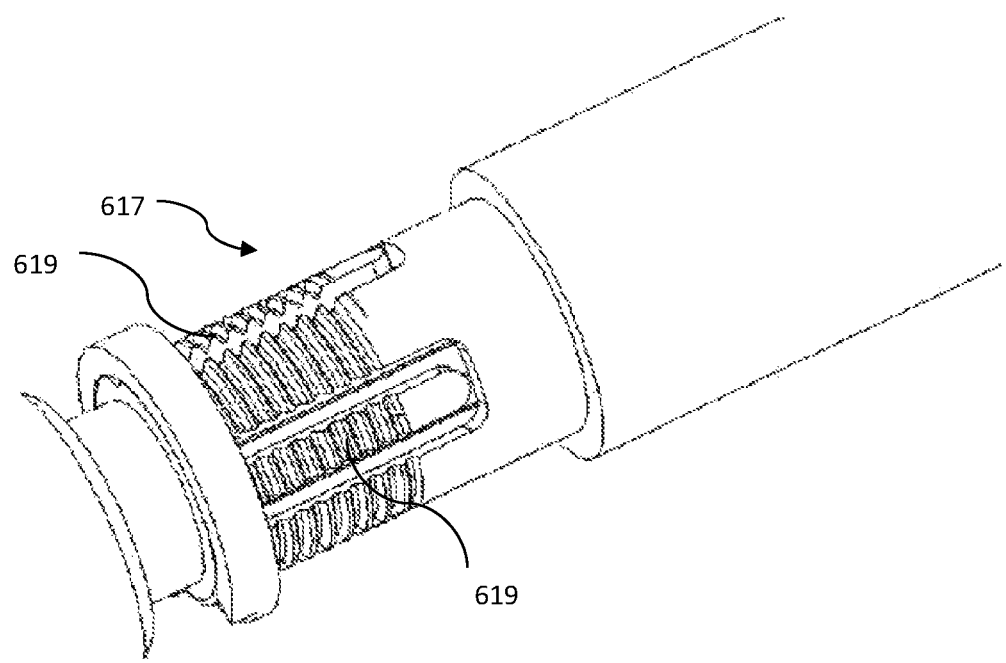

FIGS. 15 and 16 show screwdriver 600 according to another embodiment of the present disclosure. Screwdriver 600 includes locking mechanism 635 with internally threaded ring 640 which engages external threads on threaded portion 617 of outer sleeve 612. Threaded portion 617 is formed of cantilever tabs or flexible fingers 619 extending in an axial direction on threaded portion 617 and being separated along the circumference of outer sleeve 612. As threaded ring 640 is turned in a first direction, i.e. clockwise, the flexible fingers 619 flex inwardly toward the inner shaft to lock the inner shaft relative to outer sleeve 612 so that they are rotatably fixed to each other. When threaded ring 640 is rotated in a second direction, i.e. counter-clockwise, flexible fingers 619 flex outwardly away from the inner shaft to unlock the inner shaft and outer sleeve 612.

Figure 17:
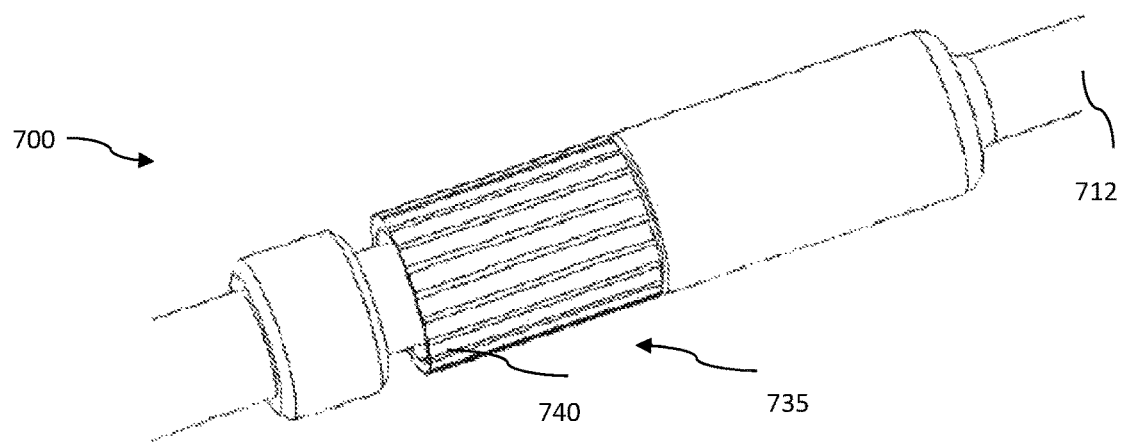
FIGS. 17 and 18 are perspective side view of another alternative locking mechanism according to an embodiment of the present disclosure.
Figure 18:
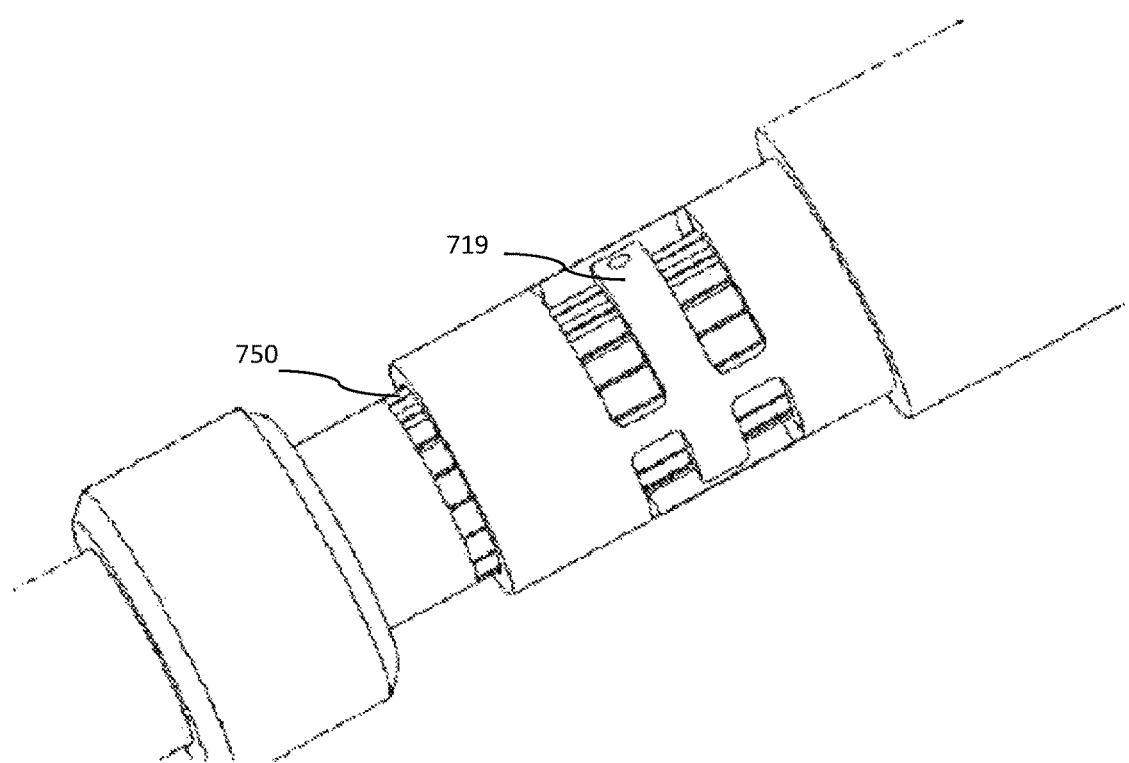
Figure 19:
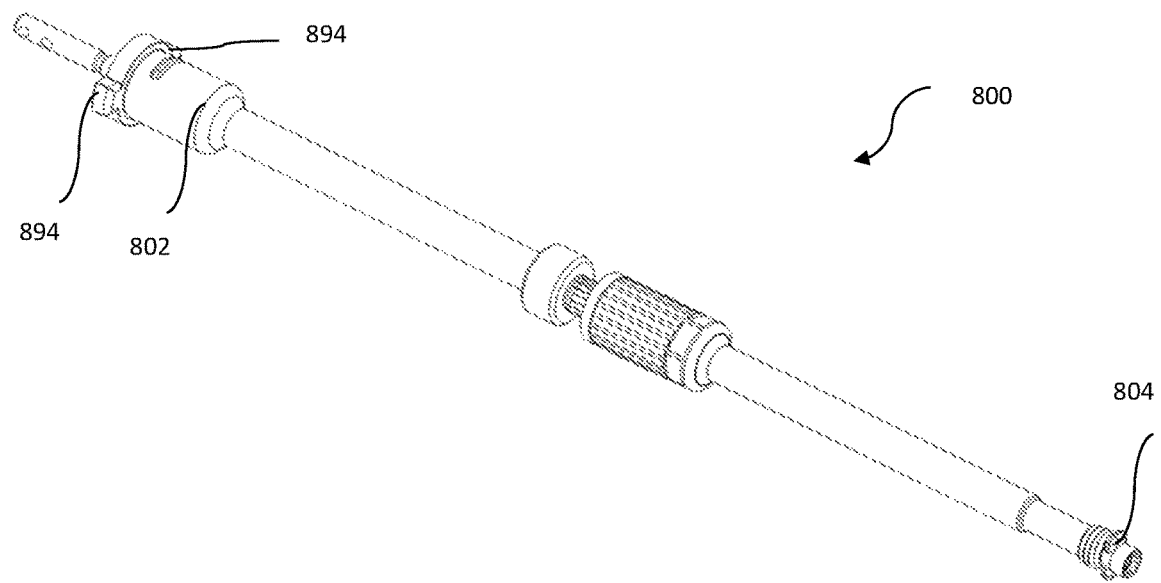
FIG. 19 is a perspective side view of a screwdriver according to an alternative embodiment of the present disclosure.
Figure 20:
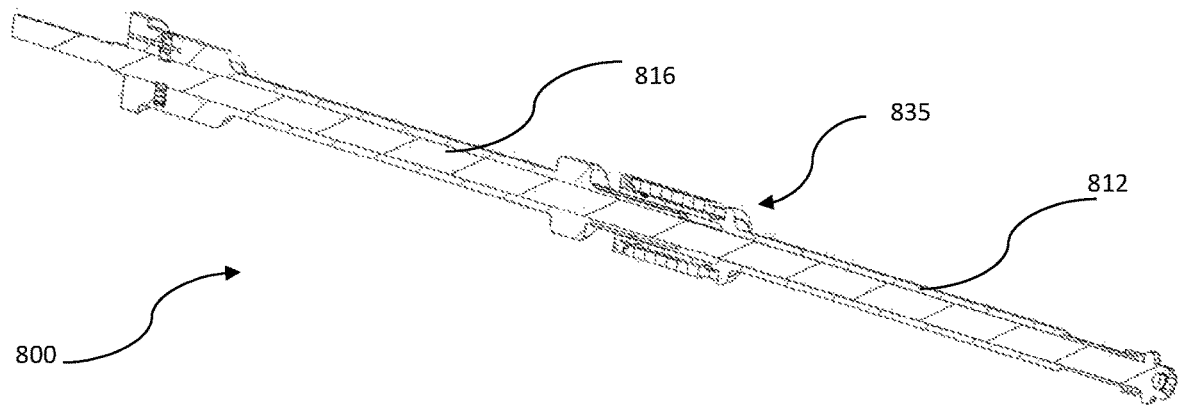
FIG. 20 is a cross-sectional view of the screwdriver of FIG. 19.

According to another embodiment of the present disclosure, screwdriver 700, shown in FIGS. 17 and 18, includes locking mechanism 735 that includes collar 740 that includes an internal cam surface. Outer sleeve 712 includes cantilevered ratchet fingers 719 extending transverse to the longitudinal axis of outer sleeve 712. Each ratchet finger 719 includes a tooth or projection (not shown) that extends inwardly toward spline member 750 and inner shaft 716. As the collar is rotated clockwise, the cam surface engages the ratchet finger 719 and pushes it toward spline member 750 so that the tooth engages spline member 750 to mechanically lock the inner shaft and outer sleeve 712. As the collar is rotated in the counter-clockwise direction, there is sufficient clearance between the inner sidewall of the collar and ratchet fingers 719 so that the fingers are not pushed toward spline member and outer sleeve 712 remains rotationally independent from the inner shaft so that screwdriver 700 is in the unlocked condition.

FIGS. 19-23 show screwdriver 800 according to another embodiment of the present disclosure. Screwdriver 800 includes many similar features to screwdriver 100, the similar features of which will not be described again herein.

At its proximal end 102, screwdriver 800 includes two torque tabs 894 for engagement with a robotic end effector, which imparts force thereon to torque the screwdriver. Further, locking mechanism includes c-clip spring 853a for biasing pawl 846 to mechanically lock inner shaft 816 and outer sleeve 812. Moreover, locking mechanism 835 includes friction drag ring 854 and to prevent unintentional unlocking or unlocking of the locking mechanism. FIG. 22 shows screwdriver 800 in the locked position with pawl 846 engaged with splines 844, and FIG. 23 shows screwdriver 800 in the unlocked position with pawl 846 disengaged from splines 844.

Figure 24:
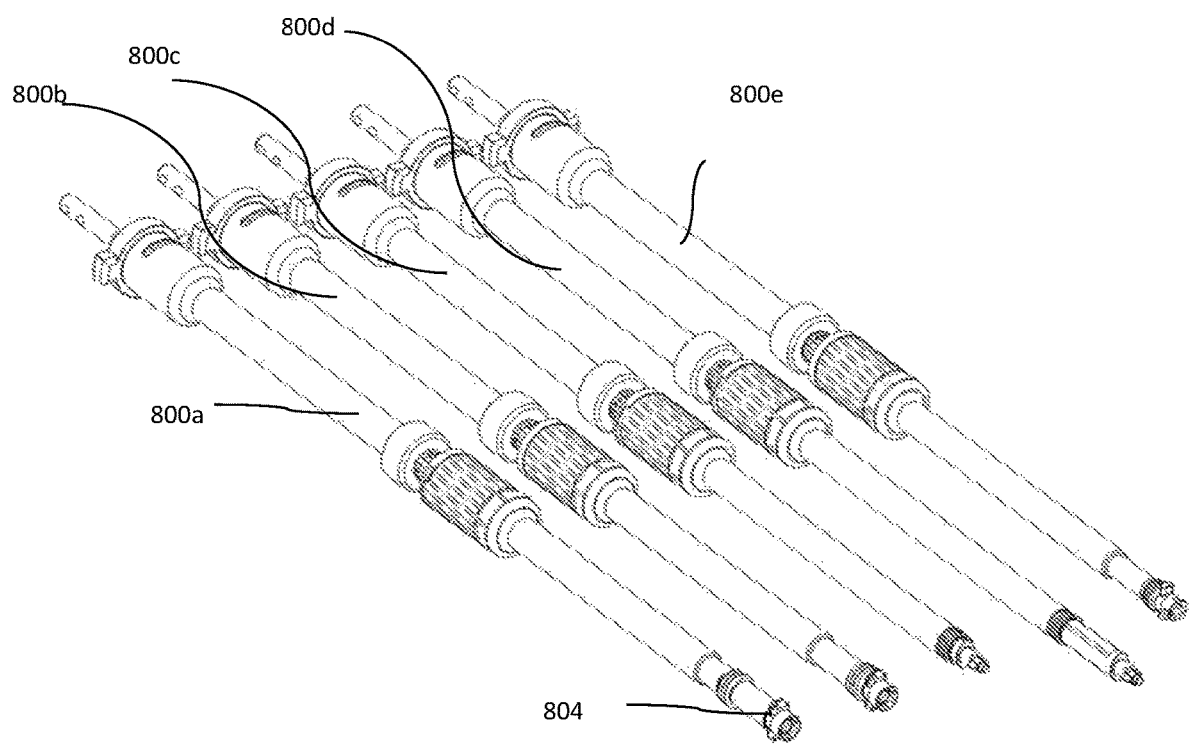
FIG. 24 is a perspective side view of various embodiments of the screwdriver 800 with distal ends for use with differing screws.

Further, distal end 804 may be adapted to conform to various types of spinal screws. For example, FIG. 24 shows screwdriver 800a for use with a standard pedicle screws, screwdriver 800b for use with minimally invasive (MIS) percutaneous pedicle screws, screwdriver 800c for use with a top-loading polyaxial pedicle screw, screwdriver 800d for break-off extension tabs for minimally invasive surgery, and screwdriver 800e for use with low profile pedicle screws. Example pedicle screws are those offered by Stryker under the names Xia® 3, ES2®, Everest®, Everest® XT and Xia® 4.5, but these screwdrivers can be utilized with other existing screws.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A screwdriver for driving a screw in bone comprising:
   a first body having first end configured to engage a tulip of the screw, a first central bore extending through the first body, and a cavity in communication with the first central bore and extending through a sidewall of the first body;
   a second body having a second central bore extending through the second body and an external surface having a spline member, the second body being positioned at least partially within the first central bore of the first body, such that the spline member is at least partially within the cavity of the first body;
   an inner shaft positioned in the first and the second central bores and having a first end configured to drive a screw into bone, the inner shaft being rotatably coupled with the second body;
   a pawl disposed within the cavity of the first body and engageable with the spline member of the second body; and
   a collar disposed on the first body and surrounding the spring-biased pawl, the collar rotatable relative to the first body and the second body and having a cammed inner surface,
   wherein when the collar is rotated in a first direction about the first body, the cammed inner surface pushes the spring-biased pawl into engagement with the spline member to rotatably couple the first body and the second body.

2. The screwdriver according to claim 1, wherein when the collar is rotated in a second direction about the first body that is opposite of the first direction, the pawl disengages from the spline member such that the second body is rotatably decoupled from the first body.

3. The screwdriver according to claim 1, wherein the pawl has a hook-shaped first end configured to engage the spline member.

4. The screwdriver according to claim 1, wherein the spline member has a plurality of axial teeth configured to engage the pawl.

5. The screwdriver according to claim 1, wherein the pawl has a sinusoidal shape.

6. The screwdriver according to claim 2, wherein the pawl defines a groove, and the screwdriver further comprises a spring received in the groove.

7. The screwdriver according to claim 6, wherein when the second body is rotatably decoupled from the first body, the screwdriver is in an unlocked condition and the spring contacts the collar.

8. The screwdriver according to claim 1, wherein when the collar is turned in the first direction, the screwdriver is in a locked condition.

9. The screwdriver according to claim 1, wherein the second body is engageable with a robotic end effector for robotic ally driving the screwdriver.

10. The screwdriver according to claim 1, wherein the first body is distal to the second body.

11. The screwdriver according to claim 1, wherein the distal body includes a screw selection button engageable with the inner shaft.

12. The screwdriver according to claim 11, wherein when the screw selection button is disengaged from the inner shaft, the first body is axially movable relative to the inner shaft.

13. The screwdriver according to claim 12, wherein the screwdriver is configured for use with reduction screws and standard screws.

14. The screwdriver according to claim 1, wherein the spring is in the form of a c-clip spring.

15. A kit comprising:
   a screwdriver for driving a screw in bone comprising:
   a first body having first end configured to engage a tulip of the screw, a first central bore extending through the first body, and a cavity in communication with the first central bore and extending through a sidewall of the first body;
   a second body having a second central bore extending through the second body and an external surface having a spline member, the second body being positioned at least partially within the first central bore of the first body, such that the spline member is at least partially within the cavity of the first body;
   an inner shaft positioned in the first and the second central bores and having a first end configured to drive a screw into bone, the inner shaft being rotatably coupled with the second body;
   a pawl disposed within the cavity of the first body and engageable with the spline member of the second body; and
   a collar disposed on the first body and surrounding the spring-biased pawl, the collar rotatable relative to the first body and the second body and having a cammed inner surface,
   wherein when the collar is rotated in a first direction about the first body, the cammed inner surface pushes the spring-biased pawl into engagement with the spline member to rotatably couple the first body and the second body; and a robot having a robotic end effector engageable with the second body for robotically driving the screwdriver.

16. The kit according to claim 15, wherein a proximal end of the screwdriver includes tabs for transmitting torque from the end effector to the screwdriver.

17. The kit according to claim 15, further comprising at least one of a standard pedicle screw and a reduction screw.

\* \* \* \* \*